United States Patent [19]

Arndt et al.

[11] Patent Number: 5,233,088
[45] Date of Patent: Aug. 3, 1993

[54] PROCESS FOR THE PREPARATION OF ALKALI METAL SALTS OF 2-PHOSPHONOBUTANE-1,2,4-TRICARBOXYLIC ACID

[75] Inventors: Uwe Arndt, Cologne; Hans-Dieter Block, Leverkusen; Roland Kleinstück, Bergisch Gladbach, all of Fed. Rep. of Germany

[73] Assignee: Bayer Aktiengesellschaft, Leverkusen, Fed. Rep. of Germany

[21] Appl. No.: 746,841

[22] Filed: Aug. 19, 1991

[30] Foreign Application Priority Data

Aug. 28, 1990 [DE] Fed. Rep. of Germany ....... 4027106

[51] Int. Cl.$^5$ .............................................. C07C 55/22
[52] U.S. Cl. .................................................... 562/594
[58] Field of Search ......................................... 562/594

[56] References Cited

FOREIGN PATENT DOCUMENTS 0059897 9/1982 European Pat. Off. .
0358022 3/1990 European Pat. Off. .

OTHER PUBLICATIONS

Cram et al., *Organic Chemistry,* 2nd Ed., McGraw-Hill Book Co., New York, p. 355 (1964).

*Primary Examiner*—José G. Dees
*Assistant Examiner*—Porfirio Nazario
*Attorney, Agent, or Firm*—Sprung Horn Kramer & Woods

[57] ABSTRACT

The present invention relates to a process for the preparation of alkali metal salts of 2-phosphonobutane-1,2,4-tricarboxylic acid, characterized in that 2-phosphonobutane-1,2,4-tricarboxylic acid penta-alkyl esters or partial esters are reacted with an aqueous alkali metal hydroxide solution in a ratio of from 0.5 to 0.76 mol, preferably from 0.6 to 0.7 mol of alkali metal hydroxide per mol of ester function at temperatures from 20° to 200° C. in a one-shot process.

11 Claims, No Drawings

PROCESS FOR THE PREPARATION OF ALKALI METAL SALTS OF 2-PHOSPHONOBUTANE-1,2,4-TRICARBOXYLIC ACID

BACKGROUND OF THE INVENTION

This invention relates to a process for the preparation of alkali metal salts of 2-phosphonobutane-1,2,4-tricarboxylic acid by alkaline saponification of the corresponding 2-phosphono-1,2,4-tricarboxylic acid pentaalkyl esters or partial esters.

It is known that phosphonic acids and their soluble salts are suitable for the sequestration of alkaline earth metal ions in aqueous systems. The following compounds are examples: Nitrilotrimethylene phosphonic acid, 1-hydroxyethane-1,1-diphosphonic acid, 1-phosphonopropane-1,2,3-tricarboxylic acid, phosphonosuccinic acid and 2-phosphonobutane-1,2,4-tricarboxylic acid (DE-A-20 61 838, EP-A-59 897).

Phosphonic acids manifest the so-called threshold effect, i.e. the formation of an insoluble precipitate of calcium carbonate in water containing lime is prevented even by the addition of one of these compounds in less than the stoichiometric quantity, based on the lime content; hence also the term "threshold inhibitors".

The possibility of commercial production of the above-mentioned phosphonic acids has been of economical interest for some time. Since some of these compounds, e.g. 1-phosphonopropane-1,2,3-tricarboxylic acid, phosphonosuccinic acid or 2-phosphonobutane-1,2,4-tricarboxylic acid, are prepared from their esters by saponification, there is also great interest in a process for converting the esters into the free acids or their alkali metal salts. The alkali metal salts are always preferred to the free acids when the threshold inhibitors are to be used in alkaline solutions or stable, storable powders are to be produced by drying.

Numerous experiments have therefore been carried out in recent times with a view to improving the conventional process for the preparation of phosphonic acids, from which the corresponding alkali metal salts are subsequently obtained by neutralisation with alkali metal hydroxide solutions, in which process the corresponding esters, in particular the methyl esters, are hydrolysed in the presence of catalytically active mineral acids or in the presence of hydrogen halide.

An important advance was achieved by the process described in DE-A-2 229 087, in which saponification is carried out at temperatures from 90° to 150° C. without the addition of foreign acids and the phosphonic acid to be produced is itself used as catalyst. The corresponding alkali metal salts are then obtained by neutralisation with alkali metal hydroxide solution after complete saponification. Disadvantages of this process are found to be the long reaction time required for complete hydrolysis, the necessity of removing the heat of neutralisation produced and, in the special case of 2-phosphonobutane-1,2,4-tricarboxylic acid, which is technically particularly important, the formation of sparingly soluble alkali metal salts of a partially neutralised 2-phosphonobutane-1,2,4-tricarboxylic acid. Other advantageous further developments of this process without the addition of foreign acid are described in DE-A-2 441 783, DE-A-2 441 878 and DE-A-2 745 982.

The object therefore arose of providing a process which could be carried out both batchwise and continuously, in which the above-described disadvantages in the preparation of soluble alkali metal salts of 2-phosphonobutane-1,2,4-tricarboxylic acid are avoided.

DESCRIPTION OF THE PREFERRED EMBODIMENTS

The present invention relates to a process for the preparation of alkali metal salts of 2-phosphonobutane-1,2,4-tricarboxylic acid, characterized in that 2-phosphonobutane-1,2,4-tricarboxylic acid penta-alkyl esters or partial esters are reacted with an aqueous alkali metal hydroxide solution in a ratio of from 0.5 to 0.76 mol, preferably from 0.6 to 0.7 mol of alkali metal hydroxide per mol of ester function at temperatures from 20° to 200° C. in a one-shot process.

Under these conditions, complete saponification can be achieved 5 to 8 times more rapidly than conventional acid catalysed saponification.

It is surprisingly found that lower as well as higher ratios are unsuitable for carrying out this process and do not lead to the required result. Against all expectations, saponification is incomplete when larger quantities of alkali metal hydroxide are used.

SUMMARY OF THE INVENTION

Alkyl esters suitable for the process according to the invention are in particular the methyl and ethyl esters as well as the esters of higher alcohols, such as propyl, butyl and pentyl esters or mixed esters of 2-phosphonobutane-1,2,4-tricarboxylic acid, such as a mixed methyl-ethyl ester.

Examples of suitable alkali metal hydroxides include potassium hydroxide and lithium hydroxide as well as sodium hydroxide.

A particularly preferred process for the preparation of alkali metal salts of 2-phosphonobutane-1,2,4-tricarboxylic acid is characterised in that the ester of 2-phosphonobutane-1,2,4-tricarboxylic acid used is the pentamethyl ester and the alkali metal hydroxide used is sodium hydroxide.

The reactions are preferably carried out under such conditions that saponification takes place at temperatures from 60° to 160° C.

The process variation in which the quantity of alkali metal hydroxide required for conversion into the tetra- or penta-alkali metal salt of 2-phosphonobutane-1,2,4-tricarboxylic acid is added after complete saponification is particularly preferred.

Processes in which hydrolysis with alkali metal hydroxide solutions is carried out at concentrations of from 10 to 45% are particularly preferred.

Reactions in which saponification is carried out under pressure proceed particularly smoothly.

Preferably the process is carried out in such a manner that saponification proceeds continuously.

For example, the 2-phosphonobutane-1,2,4-tricarboxylic acid penta-alkyl ester which is to be saponified is introduced into the reaction vessel in the form of an aqueous solution and reacted with stirring with an aqueous alkali metal hydroxide solution in a reaction ratio of from 2.5 to 3.8 mol, preferably from 3 to 3.5 mol of alkali metal hydroxide per mol of phosphonocarboxylic acid ester at temperatures from 20° to 200° C.

The above-mentioned quantities of 2-phosphonobutane-1,2,4-tricarboxylic acid penta-alkyl ester and alkali metal hydroxide solution are preferably introduced e.g. into a reaction vessel with stirrer and heated to about 100° C. Steam may then be passed through for several hours at temperatures from 100° to 130° C. and a water-alcohol mixture distilled off. The volatile constituents are condensed and the alcohol is recovered by distillation. After complete saponification, a further quantity of alkali metal hydroxide necessary for complete neutralisation of all the acid functions may be added if necessary.

The invention is further illustrated with the aid of the following Examples. The degree of saponification was determined analytically.

EXAMPLES

45% Sodium hydroxide solution is added to phosphonobutane-1,2,4-tricarboxylic acid pentmethylester in a stirred 4-liter reaction vessel in the quantity corresonding to the chosen stoichiometry (see Table 1) and the reaction mixture is heated to 110° C. 1250 g of steam per liter of reaction mixture per hour are then introduced into the reaction mixture over a period of several hours. The results of the individual experiments are shown in Table 2.

TABLE 1

| Example | Quantity of ester (g) | Quantity of NaOH solution (g) | Mol of NaOH to mol of ester | Quantity of $H_2O$ (g) |
|---|---|---|---|---|
| Example 1 | 1700 | 1333 | 3:1 | — |
| Comparison Example 1 | 1360 | 1422 | 4:1 | — |
| Comparison Example 2 | 1700 | — | — | 300 |

TABLE 2

Degree of saponification (in %) in dependence upon the saponification time

| | Saponification time (h) | | |
|---|---|---|---|
| | 0.5 | 2 | 8 |
| Example 1 | 77.6 | 94.0 | 97 |
| Comparison Example 1 | 78.0 | 79.0 | 81.0 |
| Comparison Example 2 | — | 40 | 84 |

The results of analysis entered in Table 2 show that in Example 1 substantial saponification has already taken place after 2 hours. A comparison of this result with that of Comparison Example 2, in which 2-phosphonobutane-1,2,4-tricarboxylic acid pentamethylester is saponified by the conventional process described in DE-A-2 229 087 without the addition of foreign acid, shows that in acid saponification, a degree of saponification of 84% is obtained only after 8 hours. Further, Comparison Example 1 shows that in alkaline saponification using alkali metal hydroxide in quantities outside the ratios claimed here, saponification quite unexpectedly progresses no further after a degree of saponification of 80% and complete saponification is not achieved within a comparable period of time.

It is understood that the specification and examples are illustrative but not limitative of the present invention and that other embodiments within the spirit and scope of the invention will suggest themselves to those skilled in the art.

What is claimed is:

1. A process for the preparation of alkali metal salts of 2-phosphonobutane-1,2,4-tricarboxylic acid from 2-phosphonobutane-1,2,4-tricarboxylic acid penta-alkyl esters or partial esters, characterized in that 2-phosphonobutane 1,2,4-tricarboxylic acid penta-alkyl esters or partial esters are reacted in a one shot process with an aqueous alkali metal hydroxide solution in a ratio of from about 0.5 to 0.76 mol of alkali metal hydroxide per mol of ester function at temperatures from 20° to 200° C.

2. A process according to claim 1, characterized in that the ester of 2-phosphonobutane-1,2,4-tricarboxylic acid used is the penta-methyl ester.

3. A process according to claim 1, characterized in that the alkali metal hydroxide used is sodium hydroxide.

4. A process according to claim 1, characterized in that saponification is carried out at temperatures from 60° to 160° C.

5. A process according to claim 1, characterized in that the alkyl esters are methyl or ethyl esters, which may be identical or independent of one another.

6. A process according to claim 1, characterized in that the quantity of alkali metal hydroxide required for the conversion into the tetra- or penta-alkali metal salt of 2-phosphonobutane-1,2,4-tricarboxylic acid is added after complete saponification.

7. A process according to claim 1, characterized in that hydrolysis is carried out with alkali metal hydroxide solutions at concentrations of from 10 to 45%.

8. A process according to claim 1, characterized in that saponification is carried out under pressure.

9. A process according to claim 1, characterized in that saponification is carried out continuously.

10. A process according to claim 1, characterized in that steam is passed through the reaction mixture at temperatures from 100° to 130° C. for several hours during the reaction of the two reactants, a water-alcohol mixture is distilled off, the volatile constituents are condensed and the alcohol is recovered by distillation.

11. A process according to claim 1, wherein the aqueous alkali metal hydroxide solution is present in a ratio of from about 0.6 to 0.7 mol of alkali metal hydroxide per mol of ester function.

* * * * *